(12) United States Patent
Mitariten (10) Patent No.: US 10,569,217 B2
(45) Date of Patent: Feb. 25, 2020

(54) PRODUCTION OF BIOMETHANE USING A HIGH RECOVERY MODULE

(71) Applicant: AIR LIQUIDE ADVANCED TECHNOLOGIES U.S. LLC, Houston, TX (US)

(72) Inventor: Michael J. Mitariten, Pittstown, NJ (US)

(73) Assignee: Air Liquide Advanced Technologies U.S. LLC, Houston, TX (US)

( * ) Notice: Subject to any disclaimer, the term of this patent is extended or adjusted under 35 U.S.C. 154(b) by 0 days.

(21) Appl. No.: 15/878,492

(22) Filed: Jan. 24, 2018

(65) Prior Publication Data

US 2019/0224617 A1   Jul. 25, 2019

(51) Int. Cl.
*B01D 53/22* (2006.01)
*B01D 53/26* (2006.01)
(Continued)

(52) U.S. Cl.
CPC ......... *B01D 53/226* (2013.01); *B01D 53/047* (2013.01); *B01D 53/0446* (2013.01); *B01D 53/0462* (2013.01); *B01D 53/229* (2013.01); *B01D 53/265* (2013.01); *B01D 71/52* (2013.01); *B01D 71/56* (2013.01); *B01D 71/76* (2013.01); *C07C 7/005* (2013.01); *C07C 7/12* (2013.01); *C07C 7/144* (2013.01);
(Continued)

(58) Field of Classification Search
CPC .... B01D 53/229; B01D 53/22; B01D 53/225; B01D 53/226; B01D 53/228
USPC ...................... 585/818; 95/51, 45
See application file for complete search history.

(56) References Cited

U.S. PATENT DOCUMENTS 5,709,732 A   1/1998 Prasad
5,776,990 A   7/1998 Hedrick et al.
(Continued)

FOREIGN PATENT DOCUMENTS

EP            0799634 A1 *  8/1997  ............. B01D 53/22
WO   WO 2016/107786         7/2016

OTHER PUBLICATIONS

Rabiee, et al., "Gas transport properties of reverse-selective poly (ether-b-amide6)/[Emim][BF4] gel membranes for CO2/light gases separation," Journal of Membrane Science, vol. 476, pp. 286-302 (2015).

*Primary Examiner* — Thuan D Dang
(74) *Attorney, Agent, or Firm* — Christopher J. Cronin (57) ABSTRACT

The invention relates to a process for recovering methane from digester biogas or landfill gas. More specifically, the invention pertains to biomethane production that substantially removes carbon dioxide from a digester biogas or landfill gas using first, second, and third purification stages each comprising one or more membranes selective for carbon dioxide over methane. A retentate from the first stage is separated by the one more membranes of the second stage into a second state retentate, forming a biomethane product gas. A permeate from the first stage is separated by the one or more membranes of the third stage into a third stage retentate and a third stage permeate. Recovery of methane from the biogas is boosted by feeding the third stage retentate to the first purification stage. The recovery may be optionally further boosted by compressing the second stage permeate with the biogas at a main compressor.

23 Claims, 3 Drawing Sheets

(51) Int. Cl.
  *B01D 53/04* (2006.01)
  *B01D 53/047* (2006.01)
  *B01D 71/56* (2006.01)
  *B01D 71/52* (2006.01)
  *B01D 71/76* (2006.01)
  *C07C 7/00* (2006.01)
  *C07C 7/12* (2006.01)
  *C07C 7/144* (2006.01)

(52) U.S. Cl.
  CPC .. *B01D 2256/245* (2013.01); *B01D 2257/304* (2013.01); *B01D 2257/504* (2013.01); *B01D 2257/556* (2013.01); *B01D 2257/702* (2013.01); *B01D 2257/708* (2013.01); *B01D 2257/80* (2013.01)

(56) References Cited

U.S. PATENT DOCUMENTS

| | | |
|---|---|---|
| 6,168,649 B1 | 1/2001 | Jensvold et al. |
| 6,860,920 B2 | 3/2005 | Simmons |
| 7,025,803 B2 | 4/2006 | Wascheck et al. |
| 8,999,038 B2 * | 4/2015 | Ungerank ............ B01D 53/226 95/51 |
| 2010/0107872 A1 * | 5/2010 | Bethell .................. B01D 53/04 95/92 |
| 2014/0345320 A1 * | 11/2014 | Xuan ................ B01D 53/0462 62/620 |
| 2017/0157555 A1 * | 6/2017 | Karode ................ B01D 53/225 |
| 2018/0371334 A1 * | 12/2018 | Beilfuss ................ C10G 21/27 |

* cited by examiner

PRODUCTION OF BIOMETHANE USING A HIGH RECOVERY MODULE

FIELD OF THE INVENTION

The invention pertains to the production of biomethane from biogas using gas separation membranes. More particularly, it pertains to relatively high recovery of biomethane from biogas using gas separation membranes.

BACKGROUND OF THE INVENTION

Biogas typically refers to a mixture of different gases produced from the breakdown of organic matter in the absence of oxygen in an anaerobic digestion process. Biogas can be produced from raw materials such as agricultural waste, manure, municipal waste, plant material, sewage, green waste or food waste. Biogas typically comprises as the main components 50-70% of methane ($CH_4$) and 20 to 50% carbon dioxide ($CO_2$), with lower levels of other components such as $N_2$ and $O_2$, up to 5,000 ppm or more of hydrogen sulfide ($H_2S$), siloxanes, up to 1,000-2,000 ppm of volatile organic compounds (VOC's), and is saturated with water. Biogas also includes landfill gas (LFG), which is derived from solid waste landfills that decompose to the organic waste with time, and microbe digestion of the variety of organic waste to produce methane and $CO_2$ with the wide variety of decomposition products above. In either case biogas includes high concentrations of methane and carbon dioxide, water vapor, and lesser concentrations of VOC's and other contaminants.

Specifically, digester biogas (digester gas) or landfill gas is a type of renewable energy. Methane is commonly known as natural gas and is valuable commercial commodity as a combustible fuel for supplying energy, and also as a raw material in many industrial significant processes. Thus, it is very desirable from an economic viewpoint to capture the methane from landfill or digester gas. Especially since biogas is a renewable source and not a fossil fuel.

If digester and landfill exhaust gas is not recovered, the methane escaping into ambient air presents a considerable source of air pollution. Accordingly, it is further desirable to prevent the methane emissions produced from the anaerobic digestion for environmental protection purposes. Traditionally, digester and landfill exhaust gas has been prevented from escaping to the environment by burning it in an open flame incinerator such as a flare stack. This process is inefficient. Consequently, a fraction of the methane and other obnoxious contaminants in the exhaust gas survive to pollute the ambient air. Also, common flare stack operations are a waste of the useful energy held by the methane in the exhaust gas.

Other conventional methods of recovering methane from digester and landfill exhaust gas and other sources of crude natural gas have been developed. These include gas separation processes in which the useful methane is separated from the other components of the source gas. Favored conventional gas separation processes typically utilize adsorption-regeneration technology, in which the crude gas is passed through an adsorbent material that passes selected components through the bed and adsorbs and rejects others. For example, pressure swing adsorption ("PSA") or Thermal Swing Adsorption ("TSA") technologies involve selectively adsorbing contaminants of crude gas onto adsorbent particles and allowing the so-called sweetened gas to pass through the PSA/TSA units.

Unfortunately, the adsorbent particles ultimately become saturated with the contaminants and lose ability to adsorb beyond a maximum amount. Before more contaminants can be removed from the crude, the adsorbent particles must be regenerated. This normally involves exposing the saturated particles to high temperatures and/or low pressures, and regeneration with fluids that have low concentrations of the contaminants to promote desorption of the contaminants from the particles. For example, TSA requires a supply of heat energy to heat the regeneration gas and PSA requires a supply of clean, usually low pressure gas. Additionally, adsorption-regeneration technology normally also requires support facilities for removal of water vapor, and pre-conditioning the crude gas, e.g., by compressing it to high pressure. Thus, it is very costly in financial and energy consumption aspects to operate conventional adsorption-regeneration technologies for recovering useful methane from crude natural gas and landfill exhaust gas.

On the contrary, membrane systems are versatile and are known to process a wide range of feed compositions and separations. With a very compact footprint and low weight, these membrane systems are well suited to offshore applications, remote locations, or for smaller flow rates. Recent developments in dew point control include membrane designs that can operate in condensing mode, as well as membranes that allow the simultaneous removal of water and heavier hydrocarbons from natural gas.

Membranes have been used for biogas treatment. Typical membrane processes such as those marketed by Air Liquide, involves the removal of $H_2S$ by a sulfur removal unit and a pretreatment to remove water and VOCs, followed by a two-stage membrane process that is dedicated to $CO_2$ removal.

It is also well documented that glassy polymers, such as polyimide, polyamide, polysulfone, polybenzimidazole, etc., exhibit exceptional high intrinsic $CO_2$/methane selectivity. However, the selectivity and permeance of the membranes prepared from those materials often quickly decrease once they are used for methane gas extraction in the presence of VOC's and other biogas impurities. This loss of membrane performance is caused by condensation and coating of the VOC's and siloxanes on the membrane surface. The conventional solution for this problem is to use a system including a regenerable adsorbent bed followed by a carbon trap for removing the water, siloxanes and VOCs prior to upstream of $CO_2$ removal. Although these pretreatment systems can effectively remove heavy hydrocarbons and other components from the biogas stream, the cost of the pretreatment and/or frequent membrane replacement can be prohibitive. Indeed, the cost of the pretreatment system can be as high as 50% of the total system cost (pretreatment plus membrane).

Further, the product gas produced from digester gas and landfill gas must meet safety criteria to be injected into the utility pipeline. In particular, a common industry standard aims to comply with SoCalGas® Rule 30, which sets forth the standards for utility methane gas injection in large portion of California. Specifically, according to Rule 30, the methane gas to be delivered should have:

a) Heating Value: The minimum heating value of nine hundred and ninety (990) Btu (gross) per standard cubic foot on a dry basis, a maximum heating value of one thousand one hundred fifty (1150) Btu (gross) per standard cubic foot on a dry basis.

b) Moisture Content or Water Content: For gas delivered at or below a pressure of eight hundred (800) psig, the gas shall have a water content not in excess of seven (7) pounds per million standard cubic feet. For gas delivered at a pressure exceeding of eight hundred (800) psig, the gas shall have a water dew point not exceeding 20° F. at delivery pressure.

c) Hydrogen Sulfide: The gas shall not contain more than twenty-five hundredths (0.25) of one (1) grain of hydrogen sulfide, measured as hydrogen sulfide, per one hundred (100) standard cubic feet (4 ppm). The gas shall not contain any entrained hydrogen sulfide treatment chemical (solvent) or its by-products in the gas stream.

d) Mercaptan Sulfur: The gas shall not contain more than three tenths (0.3) grains of mercaptan sulfur, measured as sulfur, per hundred standard cubic feet (5 ppm).

e) Total Sulfur: The gas shall not contain more than seventy-five hundredths (0.75) of a grain of total sulfur compounds, measured as a sulfur, per one hundred (100) standard cubic feet (12.6 ppm). This includes COS and $CS_2$, hydrogen sulfide, mercaptans and mono, di and poly sulfides.

f) Carbon Dioxide: The gas shall not have a total carbon dioxide content in excess of three percent (3%) by volume.

g) Oxygen: The gas shall not have an oxygen content in excess of two-tenths of one percent (0.2%) by volume, and customer will make every reasonable effort to keep the gas free of oxygen.

h) Inerts: The gas shall not contain in excess of four percent (4%) total inerts (the total combined carbon dioxide, nitrogen, oxygen and any other inert compound) by volume.

i) Hydrocarbons: For gas delivered at a pressure of 800 psig or less, the gas hydrocarbon dew point is not to exceed 45° F. at 400 psig, or at the delivery pressure, if the delivery pressure is below 400 psig. For gas delivered at a pressure higher than 800 psig, the gas hydrocarbon dew point is not to exceed 20° F., measured at a pressure of 400 psig.

These gas constituent limits restrict the concentration of gas impurities to protect pipeline integrity and ensure safe and proper combustion in end-user equipment. In particular, the hydrocarbon dew point requirement and the reduction of heavy hydrocarbons prevents unsafe formation of a liquid phase during transport. The hydrocarbon dew point is sensitive to small quantities of $C_{6+}$ and VOC components. As little as 450 ppm of $C_8$ hydrocarbon added to a lean gas can give it a cricondentherm of 50° F.

Further, the current methane market demands a high recovery rate from biogas of greater than 98% of methane. Many existing systems have been evaluated for modification, rather than costly replacements, to improve from 90-95% to at least 98% recovery of methane from biogas.

There are several known attempts to produce purified methane from biogas or natural gas.

U.S. Pat. No. 7,025,803 to Wascheck, et al. recovers high concentrations of methane from crude natural gas, and solid waste landfill exhaust gas uses a sequential combination of a pressure swing adsorber unit operation to remove volatile organic compounds from the crude feed gas mixture, followed by a membrane separation unit operation. While quite satisfactory in performance, the system does not satisfactorily handle relatively high levels of $H_2S$. Therefore, a separate $H_2S$ removal system (such as SulfaTreat or other treatment methods) may be required for raw biogas containing relatively high $H_2S$ levels.

US 2017/0157555 to Karode, et al. teaches purification of natural gas by removing $C_{3+}$ hydrocarbons and $CO_2$ in respective first and second gas separation membrane stages to yield conditioned gas lower in $C_{3+}$ hydrocarbons and $CO_2$ in comparison to the un-conditioned natural gas. '555 is not concerned with producing biomethane, or removing VOC's ($C_{6+}$ hydrocarbons), and siloxane from biogas. Further, product gas from natural gas sweetening typically contains a mixture of methane, ethane, and natural gas liquids.

U.S. Pat. No. 8,999,038 and WO 2016/107786, both assigned to Evonik Fibres GMBH, disclose a three-stage membrane process for $CO_2$ removal using membranes with $CO_2/CH_4$ selectivity of at least 30 without any secondary compression in between the feed and permeate stages. As disclosed, this process does not simultaneously remove sufficient amounts of $H_2S$ and $CO_2$ while achieving high methane recovery (>94%). Because the first stage permeate is not recompressed before being fed to the permeate stage, the driving force (i.e., the pressure difference between the feed and permeate sides) across the permeate stage is relatively low. A relatively low driving force necessitates a relatively greater amount of membrane surface area in both the first stage and the permeate stage, or in other words, a relatively greater number of membranes in both stages. Thus, capital costs are significantly increased. The disclosed process also requires a substantial modification if applied to an existing two-stage system. This is a very costly endeavor for customers who only wish to achieve an incremental methane recovery (in the product gas from the raw biogas) from 94% to about 98%.

U.S. Pat. No. 5,709,732 to Prasad teaches a membrane separation method for purified oxygen gas (60-90% purity) using a three-stage membrane system, wherein air is first permeated, then compressed and permeated in two subsequent membrane stages, to provide purified oxygen as a permeated gas from the third stage. Prasad does not teach or suggest a membrane system for producing methane from biogas, nor specifies the membrane composition.

U.S. Pat. No. 6,168,649 to Jensvold, et al. teaches a three membrane stage system having two compressors for purifying xenon gas from oxygen, nitrogen, carbon dioxide, or mixtures thereof, using a membrane material having high selectivity for xenon. '649 is not concerned with providing high quality methane while simultaneously removing $H_2S$, $CO_2$ and other impurities.

Therefore, there remains a need for processing biogas or landfill gas at low cost for green field projects or for improving an existing system in order to achieve high recovery of methane of at least 98%. There also remains a need for processing biogas or landfill gas at low cost that includes removal of acid gases such as $H_2S$ in order to produce methane gas suitable for utility pipeline delivery with minimal pretreatment.

SUMMARY OF THE INVENTION

There is disclosed a method of producing biomethane, comprising: separating a feed stream containing methane and impurities at a first purification stage comprising at least one membrane selective for carbon dioxide over methane into a first retentate stream and a first permeate stream; separating the first retentate stream at a second purification stage comprising at least one membrane selective for carbon dioxide over methane into a second retentate stream and a second permeate stream, the second retentate stream being biomethane; feeding the first permeate stream to a high recovery module comprising a second compressor and a third purification stage comprising one or more membranes in series or in parallel; compressing the first permeate stream at the secondary compressor; separating the compressed first permeate stream at the third purification stage into a third retentate stream and a third permeate stream; and combining the third retentate stream with the combined stream to form the feed stream.

There is also provided an installation for producing biomethane containing at least 94% methane, comprising: a source of a biogas; a main compressor, an inlet of which is in fluid communicating with the source; a first purification stage comprising at least one membrane selective for carbon dioxide over methane, an inlet of the first purification stage being in fluid communication with an outlet of the main compressor; a second purification stage comprising at least one membrane selective for carbon dioxide over methane, an inlet of the second purification stage being in fluid communication with a retentate outlet of the first purification stage; and a high recovery module comprising a third purification stage comprising one or more membranes in series or in parallel that are selective for carbon dioxide over methane and a secondary compressor that is in fluid communication between a permeate outlet of the first purification stage and an inlet of the third purification stage, wherein a retentate outlet of the third purification stage is in fluid communication with the first purification stage inlet so as to allow a retentate stream from the third purification stage to be recycled to the first purification stage.

There is also provided a method for increasing a recovery of methane in biomethane product gas produced by an existing installation for producing biomethane comprising a source of a biogas, a main compressor, a first purification stage comprising at least one membrane selective for carbon dioxide over methane, a second purification stage comprising at least one membrane selective for carbon dioxide over methane, an inlet of the main compressor being in fluid communication downstream of the source, an inlet of the first purification stage being in fluid communication downstream of an outlet of the main compressor, an inlet of the second purification stage being in fluid communication downstream of a retentate outlet of the first purification stage, a permeate outlet of the second purification stage being in fluid communication with the inlet of the main compressor, said method comprising the steps of: providing a high recovery module comprising a secondary compressor and a third purification stage comprising at least one membrane selective for carbon dioxide over methane; placing an inlet of the secondary compressor in downstream flow communication with a permeate outlet of the first purification stage; placing an inlet of the third purification stage in downstream flow communication with an outlet of the secondary compressor; and placing a retentate outlet of the third purification stage in fluid communication with the inlet of the first purification stage.

Any one or more of the above methods and installation may include one or more of the following aspects:

the second permeate stream and a raw biogas stream are fed to a main compressor and compressed so as to form a combined stream, the raw biogas stream comprising 40-75% methane and impurities of: greater than 0% and up to 10% nitrogen, greater than 0% and up to 3% oxygen, 20-55% carbon dioxide, greater than 0 ppm and up to 5,000 ppm hydrogen sulfide, 0 to 100 ppm siloxanes, greater than 0 ppm and up to 1,000-2,000 ppm of $C_{6+}$ hydrocarbons and VOCs, and greater than 0% water.

the first retentate stream comprises at least 60% methane, the first permeate stream comprises less than 20% methane, the second retentate stream comprises at least 94% methane, the second permeate stream comprises less than 80% methane, the third retentate stream comprises at least 40% methane and the third permeate stream comprises less than 3% methane.

an amount of water is removed from the combined stream at a dehydration unit or through cooling after compression prior to combination with the third retentate stream.

the second permeate stream and a raw biogas stream are fed to a main compressor and compressing them so as to form a combined stream and the feed stream is formed by combining the third retentate stream with the combined stream, wherein the second permeate stream comprises at least 40% methane, at least 20% carbon dioxide, less than 1,000 ppm hydrogen sulfide, less than 1000 ppm of $C_{6+}$ hydrocarbons, VOCs and siloxane, and less than 0.05% water and the first permeate stream comprises 5-15% methane, greater than 0 ppm but up to 10,000 ppm of $H_2S$, greater than 0% but up to 3% water, and up to 95% $CO_2$.

after water removal at the dehydration unit and prior to combination with the third retentate stream, $H_2S$ levels in the combined stream are reduced to less than 4 ppm using $H_2S$ scavenger media.

the combined stream is fed to an adsorption-based purification unit where amounts of C6+ hydrocarbons present in the combined stream are removed by the adsorption-based purification unit, the adsorption-based purification unit comprising an adsorbent bed, the adsorption-based purification unit being selected from the group consisting of a non-regenerative media unit, a pressure swing adsorption unit, a temperature swing adsorption unit, and a pressure-temperature swing adsorption unit; and optionally, when the adsorption-based purification unit is a pressure swing adsorption unit, a temperature swing adsorption unit or a pressure-temperature swing adsorption unit, the adsorption bed is regenerated with the third permeate stream.

the third purification stage comprises a first group of one or more membranes that is in series with a second group of one or more membranes, the first permeate stream is separated by the first group into an intermediate retentate stream and an intermediate permeate stream, and the intermediate retentate stream is fed to the second group where it is separated into the third permeate stream and the third permeate stream.

each of said at least one membrane of said first purification stage comprises a porous polymeric substrate having at least one separation layer, the substrate being selected from the group consisting of polyimides, poly sulfones, polyether ether ketones, and mixtures thereof.

the separation layer is made of a copolymer or block polymer of the formula:

where PA is an aliphatic polyamide having 6 or 12 carbon atoms and PE is either poly(ethylene oxide) or poly(tetramethylene oxide).

the separation layer is made of repeating units of the following monomers:

the separation layer is made of a copolymer or block polymer of tetramethylene oxide, propylene oxide, and/or ethylene oxide.

the at least one membrane of the first purification stage is selective for $H_2S$, $C_{6+}$ hydrocarbons, carbon dioxide, siloxane and water over methane.

the at least one membrane of the second purification stage is comprised of a material selected from the group consisting of cellulose acetate, a polysulfone, a polyimide, and mixtures thereof.

the at least one membrane of the second purification stage is selectivity for carbon dioxide over methane.

a pressure differential over the membrane between the first permeate stream and the feed stream is at least 50 psig, and preferably at least 200 psig.

the second permeate stream comprises at least 40% methane, at least 20% carbon dioxide, less than 1,000 ppm hydrogen sulfide, less than 1000 ppm of $C_{6+}$ hydrocarbons and siloxane, and less than 0.05% water.

the second permeate stream and a raw biogas stream are compressed at a main compressor so as to form a combined stream and the feed stream is formed by combining the third retentate stream with the combined stream, wherein the raw biogas stream has a methane concentration of 40-75% and at least 98% of methane in the raw biogas stream is recovered in the second retentate stream.

the first permeate stream comprises 5-15% methane, greater than 0 ppm but up to 10,000 ppm of $H_2S$, greater than 0% but up to 3% water, and up to 95% $CO_2$.

the third permeate stream is flared or vented.

the at least one membrane of the third stage is the same as the at least one membrane of the first stage or the second stage.

the product gas is comprised of at least 94% methane, below 3% of $CO_2$, below 150 ppm of $H_2S$, below 100 ppm of VOC's, and below 0.01% of $H_2O$.

amounts of $H_2S$ are removed from the second retentate stream with a $H_2S$ scavenger media so as to achieve a $H_2S$ concentration in the second retentate stream of less than 4 ppm of $H_2S$.

a permeate outlet of the second purification stage is in fluid communication with the main compressor inlet so as to allow a permeate stream from the second purification stage to be recycled to the main compressor.

a dehydration unit is in fluid communication between the main compressor outlet and the first purification stage inlet that is adapted and configured to remove amounts of water from a combination stream received from the compressor outlet prior to the combination stream being fed to the first purification stage inlet.

the dehydration unit is a condenser or dehydration media.

a $H_2S$ removal unit comprising a $H_2S$ scavenger media is in fluid communication between the main compressor and the first purification stage, the $H_2S$ removal unit being adapted and configured to remove amount of $H_2S$ from a combination stream received from the compressor.

a $H_2S$ removal unit comprising a $H_2S$ scavenger media is in fluid communication prior to the inlet of the main compressor the $H_2S$ removal unit being adapted and configured to remove amount of $H_2S$ from the raw feed gas prior to the combination stream delivered to the compressor inlet.

the high recovery module further comprises a fourth purification stage comprising at least one membrane selective for carbon dioxide over methane; an inlet of the fourth purification being in downstream flow communication with a retentate outlet of the third purification stage; a permeate outlet of the second purification stage is in fluid communication with the main compressor inlet so as to allow a permeate stream from the second purification stage to be recycled to the main compressor; and a retentate outlet of the fourth purification stage is in fluid communication with the first purification stage inlet so as to allow a retentate stream from the fourth purification stage to be recycled to the first purification stage.

DETAILED DESCRIPTION OF THE INVENTION

The present invention is directed towards a novel process of producing biomethane from biogas with improved recoveries of biogas methane in the biomethane product gas. A raw biogas stream may optionally be dehydrated, pretreated to remove impurities, and compressed.

Whether combined with one or more gases, the raw biogas stream is ultimately fed to a first purification stage that includes one more gas separation membranes (typically polymeric membranes) each of which is selective for carbon dioxide over methane. At the first purification stage, the feed stream (ordinarily at a pressure of about 150-200 psig) is separated into a first permeate stream (ordinarily at a pressure of about 1-15 psig, more typically about 1-7 psig) and a first retentate stream. The first retentate stream (which is at a pressure often around 10 psig lower than that of the feed stream) is fed to a second purification stage including one or more gas separation membranes (again typically polymeric membranes) each of which is also selective for carbon dioxide over methane. At the second purification stage, the first retentate stream is separated into a second permeate stream (ordinarily at a pressure of around 0-7 psig) and a second retentate stream (ordinarily at a pressure about 10 psig lower than that of the first retentate stream). Whether the second retentate stream is optionally treated for further removal of impurities, the second retentate stream constitutes the biomethane product.

The first permeate stream typically comprises at least 5% (often 5-15%) methane, up to 10,000 ppm of $H_2S$, up to 3% water, and up to 95% $CO_2$. In order to recover amounts of methane present in the first permeate stream that might otherwise not be recovered, it is fed to a high recovery module that includes a (secondary) compressor and a third purification stage that includes one or more gas separation membranes (typically polymeric membranes) in parallel or in series, each of which is selective for carbon dioxide over methane. At the third purification stage, the first permeate stream is compressed by the secondary compressor (ordinarily to a pressure about 10 psig higher than that of the feed gas fed to the first purification stage) is separated into a third permeate stream and third retentate stream (which is at a same pressure as that of the feed gas fed to the first purification stage). While the third permeate stream is ordinarily at a pressure as low as 0-1 psig in the case of rejection by flaring or thermal oxidation, it is typically at a pressure of about 3-6 psig when it is used to regenerate an adsorbent bed (as describe below). Because valuable amounts of methane (typically 50-75%) are present in the third retentate stream, it is fed back to the first purification stage. Because the third retentate stream is already at a relatively high pressure (by virtue of the first permeate stream being compressed in the high recovery module), it need not be recompressed.

In one embodiment, the third purification stage may include a first group of one or more membranes which separate the first permeate stream into an intermediate retentate stream and an intermediate permeate stream. The third purification stage also includes a second group of one or more membranes in series that receive the intermediate retentate from the first group and separate it into the third permeate stream and the third retentate stream. This particular embodiment is advantageous because the intermediate permeate stream contains very high amounts of $CO_2$ and may be recovered as a useful product gas containing as much as 96% $CO_2$. The third permeate stream, which is quite low in methane, may be vented or flared.

The second permeate stream typically comprises at least 40% methane, at least 20% $CO_2$, below 1,000 ppm of $H_2S$, below 1,000 ppm of VOC's and below 0.05% of $H_2O$. Optionally, in order to recover additional amounts of methane present in the second permeate stream, the second permeate stream may be fed to the compressor upstream of the first purification where the second permeate stream and the raw biogas stream are compressed.

Raw biogas from a landfill or digester is ordinarily pressurized a little above atmospheric pressure. Assuming that it is not otherwise provided at relatively higher pressures, it may optionally be compressed by a main compressor, typically to a pressure of about 150-200 psig. The compressed raw biogas is then cooled and amounts of condensed water are removed via phase separation and/or with a dehydration media.

Before it is combined with the third retentate stream (and optionally after it has been combined with the second permeate stream) and fed to the first purification stage, the raw biogas may be optionally processed to remove impurities. For example, the $H_2S$ levels of the raw biogas (or combined raw biogas and third stage retentate) may be lowered by passing the biogas through a $H_2S$ removal unit that includes $H_2S$ scavenger media. In addition to, or as an alternative to such purification of the raw biogas (or combined raw biogas and third stage retentate), $H_2S$ may be removed from the second retentate stream by an $H_2S$ removal unit.

Also, before the raw biogas is combined with the third retentate stream (and optionally after it has been combined with the second permeate stream) and fed to the first purification stage, VOCs such as $C_{6+}$ hydrocarbons may be removed from the raw biogas (or the combined raw biogas and third stage retentate) with an adsorption-based purification unit (containing an adsorbent bed) such as a one having a non-regenerative media bed, a pressure swing adsorption unit, a temperature swing adsorption unit, or a pressure-temperature swing adsorption unit. In any of these cases, the adsorbent bed may be regenerated with a regeneration gas such as air or optionally the third stage permeate stream may be used as a regeneration gas.

In addition to, or instead of, use of the third stage permeate stream as a regeneration gas, the third stage permeate stream may be vented, flared, thermally oxidized at a thermal oxidation unit, or recovered as a useful $CO_2$ product gas.

Each of the first, second, and third purification stages is selective for carbon dioxide over methane. This means that a stream of gas fed to such a purification stage will produce a permeate stream (from the associated one or more gas separation membranes of that purification stage) and a retentate stream (from the associated one or more gas separation membranes of that purification stage) where the permeate is enriched in carbon dioxide and deficient in methane compared to the associated retentate stream. This leaves open the possibility to include one or more gas separation membranes in the first stage, in the second stage, and/or in the third stage that is selective for methane over carbon dioxide. While this is not typically preferred, there may be an advantage to include one or more membranes that are highly selective for one or more impurities despite the fact that they may otherwise permeate more methane than desired. Optionally, the membranes may also be selective for $H_2S$ over methane, for $C_{6+}$ hydrocarbons over methane, and/or for water over methane.

As used herein, the term "biogas" typically refers to a mixture of different gases produced from the breakdown of organic matter in the absence of oxygen in an anaerobic digestion process. Biogas can be produced, such as in an aerobic digester, from raw materials such as agricultural waste, manure, municipal waste, plant material, sewage, green waste or food waste. As the main components, biogas typically comprises 50-70% methane and 20 to 50% carbon dioxide. Biogas includes lower levels of other components such as $N_2$ and $O_2$ (typically from air infiltration), up to 5,000 ppm or more of hydrogen sulfide ($H_2S$), may contain measurable amounts of siloxanes, up to 1,000-2,000 ppm of volatile organic compounds (VOC's). It is also typically saturated with water. Biogas also includes landfill gas (LFG), which is derived from solid waste landfills that decompose to organic waste with time, and microbe digestion of a variety of the organic waste to produce methane and $CO_2$ with the wide variety of other components described above. In either case, biogas includes high concentrations of methane and carbon dioxide, water vapor, and lesser concentrations of VOC's and other contaminants The composition of the biogas sourced from a digester gas or landfill gas varies depending upon the substrate composition, as well as the conditions within the anaerobic reactor (temperature, pH, and substrate concentration). The biogas or landfill gas of the present invention is entirely distinct from natural gas extracted from a subterranean or subsea geological formation, or that of a producing well. Specifically, the digester biogas or landfill gas of the present invention is essentially free from butane, ethane and propane.

As used herein, the term "biomethane" refers to renewable natural gas (RNG) or biomethane. It is a pipeline-quality gas that is interchangeable with conventional natural gas and, thus, can be used in natural gas vehicles. Biomethane is essentially biogas that has been processed to purity standards. Like conventional natural gas, biomethane can be used as a transportation fuel in the form of compressed natural gas (CNG) or liquefied natural gas (LNG). Biomethane qualifies as an advanced biofuel under the Renewable Fuel Standards. For the present invention, biomethane is the product gas that fits the requirements of SoCal Gas® Rule 30 or the requirements of the delivery pipeline (when it is injected into a natural gas pipeline) or the requirements of the CNG station (when it is provided to a CNG station). It has at least 94%, preferably at least 98% methane, less than 3% carbon dioxide, and less than 100 ppm $H_2S$, water, and VOC's (such as $C_{6+}$ hydrocarbons).

Membranes of the First Stage

The membranes of the first stage are selective for carbon dioxide over methane. They are typically also relatively highly selective for $H_2S$ over methane. The membrane may be asymmetric or composite, in which case one or more separation layers is supported by a porous support. In the case of composite membranes, the substrate is often a polyimide, polysulfone, and polyether ether ketone, and typically a polyether ether ketone. The separation layer performs the desired separation while the substrate provides mechanical strength. The membranes of the first stage typically have a specific surface area above 20 $m^2/g$, preferably above 100 $m^2/g$, and a pore size of below 1 micrometer, preferably below 0.25 micrometer, and more preferably below 0.015 micrometer. The membrane is in the form of a flat film, or as a plurality of hollow fibers. The first purification stage typically has a $CO_2$ to methane selectivity of 5-40.

In the context of hollow fibers, the separation layer is configured as a sheath surrounding a core made of the support layer. In the case of hollow fibers, the fiber preferably possesses an outside diameter from about 50 to about 50,000 micrometers, more preferably from about 80 to about 1,000 micrometers, with a wall thickness from about 10 to about 1,000 micrometers, preferably from 20 to 500 micrometers. In the case of film, the film preferably possesses a thickness of from about 10 to about 1,000 micrometers, most preferably from about 25 to about 500 micrometers. The film may be optionally supported by a permeable cloth or a screen.

Figure 3:
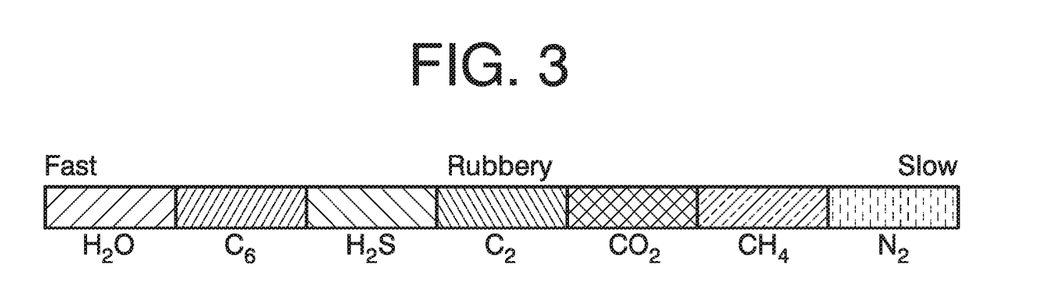
FIG. 3 illustrates relative permeation rates for rubbery membranes.
Figure 4:
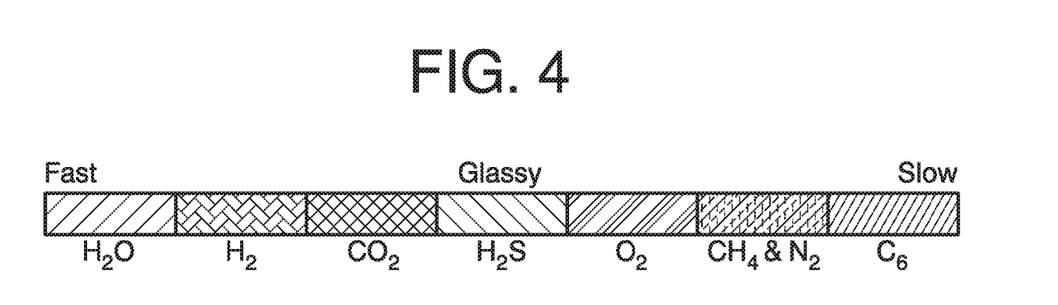
FIG. 4 illustrates relative permeation rates for glassy membranes.

Skilled artisans will recognize that the dense outer layer of an asymmetric membrane or the separation layer supported by a support layer (hereinafter "separation layer") may be made of a glassy or rubbery polymer. The relative rates of permeation for common gases through rubber membranes and glassy membranes are graphically illustrated in FIG. 3 (rubbery membranes) and FIG. 4 (glassy membranes). Optionally, the membranes of the first stage are made of rubbery membranes as rubbery membranes exhibit satisfactory resistance to degradation upon exposure to benzene, toluene, and xylene (BTX), water, mercaptans, or acid gases. Rubbery membranes preferentially permeate water, $H_2S$, $CO_2$ and/or heavy hydrocarbons and VOCs from high pressure to low pressure, leaving behind, at relatively high pressure, a water, $H_2S$, carbon dioxide, and VOC-lean retentate that is enriched in methane, typically with less than about 0.1% of water. As a result, there is no need for recompression of the first retentate stream before it is fed to the second stage. Typically, the pressure drop between the feed gas (in the case of the first stage) and the retentate gas is less than 50 psi (3.45 bar), preferably less than 30 psi (2.07 bar), or more preferably less than 20 psi (1.38 bar).

Particular types of rubbery polymers for separation layer include the copolymer or block polymer of the formula:

where PA is an aliphatic polyamide having 6 or 12 carbon atoms and PE is either poly(ethylene oxide) poly(tetramethylene oxide). These copolymers are commercially available as poly(ether-b-amide) multiblock copolymers from Arkema under the trade name of PEBAX®, and poly(butylene terephthalate) ethylene oxide copolymer available under the trade name of Polyactive®. Typically, the PEBAX polymers from Arkema include PEBAX 7233, PEBAX 7033, PEBAX 6333, PEBAX 2533, PEBAX 3533, PEBAX 1205, PEBAX 3000, PEBAX 1657, or PEBAX 1074. PEBAX 1657 exhibits a methane permeability of 5.12; see Barrer. H. Rabiee, et al., *J. Membrane Sci.* vol. 476, pp. 286-302 (2015).

Another type of rubbery polymer for the separation layer include those made of repealing units of the following monomers, also known as Polyactive® multiblock copolymers:

Other suitable polymers for separation layer include those made of a copolymer or block polymer of tetramethylene oxide, and/or propylene oxide, or ethylene oxide. These copolymers or block polymers of tetramethylene oxide, and/or propylene oxide, or ethylene oxide may be conveniently synthesized, such as the polyester ether disclosed in U.S. Pat. No. 6,860,920, the polyester ethers of which are incorporated by reference;

wherein PE may be one or more of the following structures:

Other copolymers or block polymers of tetramethylene oxide, and/or propylene oxide, or ethylene oxide may be conveniently synthesized, such as polyimide ether disclosed in U.S. Pat. No. 5,776,990, the polyimide ethers of which are incorporated by reference. The copolymers can be further obtained by copolymerization of acrylated monomers containing oligomeric propylene oxide, ethylene oxide, or tetramethyelene oxide.

The membrane is robust and is operable with coalescing filters in the condensing environments.

Alternatively, the separation layer may be made of a glassy polymer. Common glassy polymers for the membrane separation layer include cellulose acetate, polysulfones, and polyimides. Polyimides essentially consists of repeating units of dianhydride-derived units of formula (I) and diamine-derived units

(I)

Each R is a molecular segment independently selected from the group consisting of formula (1), formula (2), formula (3), and formula (4):

(1)

(2)

(3)

(4)

Each Z is a molecular segment independently selected from the group consisting of formula (5), formula (6), formula (7), formula (8), and formula (9).

(5)

(6)

(7)

(8)

(9)

Each diamine-derived unit is a diamine-derived moiety independently selected from the group consisting of formula (A), formula (B), formula (C), formula (D), formula (E), formula (F), formula (G), and formula (H):

(A)

(B)

(C)

(D)

(E)

(F)

(G)

(H)

Each X, $X_1$, $X_2$, $X_3$, $X_4$, $X_5$, $X_6$, $X_7$, and $X_8$ is independently selected from the group consisting of hydrogen, an aromatic group, and a straight or branched $C_1$ to $C_6$ alkyl group. Each $R_a$ is a straight or branched $C_1$ to $C_6$ alkyl group having either a terminal hydroxyl group, a terminal carboxylic acid group, or a terminal carbon to carbon double bond. Each Z' is a molecular segment selected from the group consisting of formula (a), formula (b), formula (c), and formula (d):

Each Z" is a moiety selected from the group consisting of formula (U) and formula (V):

Each $X_9$ is selected from the group consisting of hydrogen, a straight or branched alkyl group having 1 to 6 carbon atoms, and a straight or branched perfluoroalkyl group having 1 to 6 carbon atoms.

Alternatively, the separation layer in the first stage, the membranes are of a mixture of rubbery and glassy membrane.

Suitable hollow fiber membranes for the first stage are commercially available from Air Liquide Advanced Technologies, US.

Membranes of the Second Stage

While the membranes of the second stage may have a separation layer made of a glassy or rubbery polymer, typically the separation layer is made of a glassy polymer, non-limiting members of which cellulose acetate, polysulfones, polyamides, and polyimides as described above. Glassy membranes often exhibit superior $CO_2$ rates.

In one particular embodiment, rubbery membranes available from Air Liquide Advanced Technologies, US are used for the first stage while glassy membranes available from Air Liquide Advanced Technologies, US are used for the second stage. Those skilled in the art will recognize that "rubbery membranes" refers to membranes having a rubbery separation layer while "glassy membranes" refers to membranes having a glassy separation layer. This particular combination of membranes for the first and second stages exhibits several advantages. While the carbon dioxide/methane selectivity of the first stage may not be as high as that of the second stage, the relatively high flux of carbon dioxide, $H_2S$, $C_{6+}$ hydrocarbons, and water allows the production of a more purified first retentate stream, even if it comes at the cost of losing some of the methane (in comparison to a glassy polymer) to the first permeate stream. On the other hand, since the $H_2S$, $C_{6+}$ hydrocarbons, and water are largely removed by the first stage, the superior carbon dioxide/methane selectivity of the second stage allows the production of a second stage permeate stream (i.e., the biomethane product gas) having a relatively high methane purity.

High Recovery Module ("HRM")

The HRM includes a (secondary) compressor and a third purification stage comprising one or more membranes in parallel or in series.

Because the HRM compressor receives far less gas than any main compressor that is used to compress the raw biogas, and can have a higher suction pressure, a much smaller compressor for the HRM may be used. As a result, the capital expense (i.e., the sales price of the compressor) and the operating expense (i.e., the electrical energy consumed by the compressor) are far lower than those of any main compressor. Because the first permeate stream is compressed by the secondary compressor before being separated by the membranes of the third stage, the third stage retentate stream has a relatively high pressure, thereby allowing it to be fed to the first stage without first being compressed by the main compressor. As a result, the capital expense and size of the main compressor and the operating expense and energy consumed by the main compressor may be correspondingly decreased.

Similar to those of the first and second stages, the membranes of the third purification stage may include a separation layer made of either rubbery or glassy polymers, including those described above. Because the first permeate stream (fed to the HRM) has a much smaller mass flow rate than those of the feed gas stream (fed to the first stage) and the first retentate stream, skilled artisans will recognize that the total surface area of (i.e., the number of) membranes used in the third stage is significantly lower than those in each of the first and second stages.

As the name suggests, the HRM helps boost the recovery of methane (from the raw biogas) realized in the biomethane product gas to 98% or higher. It also can produce a third permeate gas with a relatively high carbon dioxide concentration of 96% or more.

Retrofitting a Two-Stage Membrane System with a HRM

Instead of a full replacement of an existing two-stage membrane purification system for producing biomethane from biogas, a HRM can be added onto an existing two-stage gas separation membrane system so as to boost recovery of methane from the raw biogas while producing a biomethane product gas containing at least 94% methane. Specifically, an existing two-stage membrane purification system includes a first purification stage (that includes one or more membranes selective for carbon dioxide over methane) which separates a feed stream of raw biogas stream (or optionally also including a permeate stream from a downstream purification stage) into a first permeate stream and a first retentate stream. The existing system also includes a second purification stage (that includes one or more membranes selective for carbon dioxide over methane) that separates the first retentate stream into a second permeate stream and a second retentate stream that ordinarily constitutes biomethane product gas. The materials that the membranes are comprised of may be those of the first and second stages as described above. An HRM (comprising a secondary compressor and a third purification stage comprising one or more membranes in parallel or in series) is integrated with the existing system by fluidly connecting a permeate outlet of the first stage with an inlet of the third stage. A retentate outlet of the third stage is fluidly connected to an inlet of the first stage. In operation, the first permeate stream is compressed by the secondary compressor of the HRM and fed to the one or more membranes of the third stage where it is separated into a third permeate stream and third retentate stream. The methane recovery of the existing system is boosted by the fact that the methane otherwise lost in the first permeate stream is recovered by the HRM and recycled to the first stage where much of the recovered methane is retained as a first stage retentate stream.

Biomethane Production

I will now proceed to describe particular embodiments.

Figure 1:
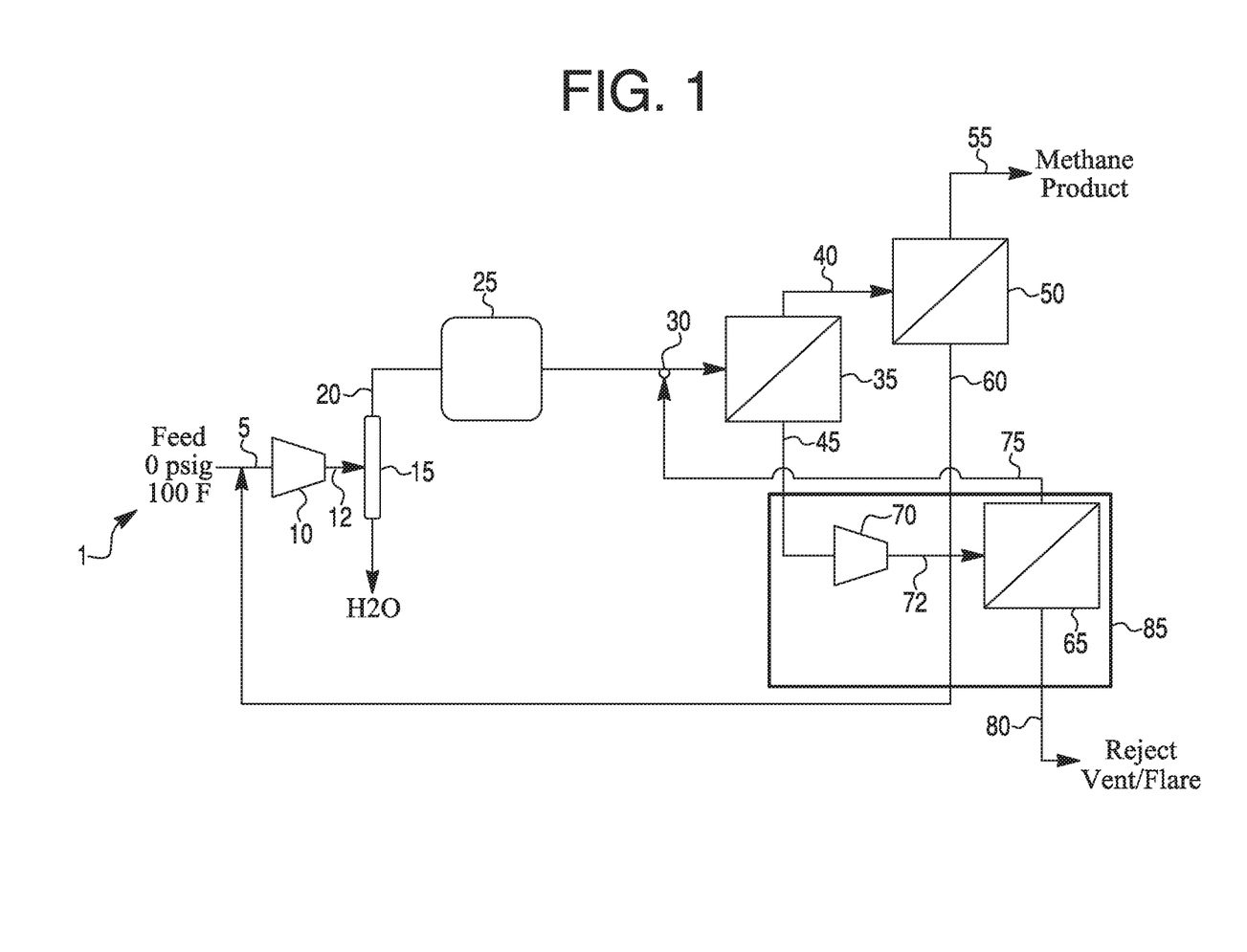
FIG. 1 illustrates a first embodiment of biomethane production containing a high recovery module and a $H_2S$ removal media.

As best illustrated in FIG. 1, a raw biogas feed 1 of primarily methane and carbon dioxide and including up to about 5,000 ppm $H_2S$ at 100° F. is compressed in a main compressor 10 along with a second stage permeate stream 60 so as to provide a compressed combined feed 12. If desired, the water level of the combined feed 12 is optionally reduced by a condenser 15 which cools the combined feed 12. The resultant condensed water is removed by phase separation, thereby producing a dried, combined feed 20, typically at a pressure of 150-200 psig. Alternatively, the water level may be reduced with a dehydration media. Also if desired, $H_2S$ levels in the dried, combined feed 20 may be subsequently lowered using an $H_2S$ removal media 25. After this optional $H_2S$ treatment, stream 20 is combined with a retentate stream 75 from the HRM 85 to form a feed stream 30.

The feed stream 30 is fed to a first purification stage 35 which includes one or more gas separation membranes (glassy or rubbery) that are selective for water, $H_2S$, and carbon dioxide over methane (and in the case of rubbery membranes, selective for $C_{6+}$ hydrocarbons over methane). The feed stream 30 is separated by the first purification stage 35 into a first stage retentate stream 40 and a first stage permeate stream 45 that is deficient in methane but enriched in carbon dioxide, water and other impurities such as $H_2S$ in comparison to the first stage retentate stream.

The first stage retentate stream 40 is subsequently fed to a second purification stage 50 which includes one or more glassy gas separation membranes that are selective for water, $H_2S$, and carbon dioxide over methane and for methane over $C_{6+}$ hydrocarbons. The first stage retentate stream 40 is separated by the second purification stage 50 into a second stage retentate stream 55 and a second stage permeate stream 60 that is deficient in methane but enriched in carbon dioxide and water in comparison to the second stage retentate stream 55. The second stage retentate stream 55 constitutes the biomethane product gas. Typically at about 150 psig, the second stage retentate stream 55 has at least 94% methane and contains 150 ppm or less of $H_2S$. While the second stage permeate stream 60 contains less than 80% methane and also contains significant amounts of carbon dioxide, it still contains a valuable amount of methane and is preferably recycled back to an inlet 5 of the main compressor 10 for compression with the raw biogas stream 1.

The first permeate stream 45, typically at a relatively low pressure such as about 2 psig, is fed to the HRM 85 where it is compressed by a secondary compressor 70 to produce a compressed first permeate stream 72. The compressed first permeate stream 72 is then fed to a third purification stage 65 where it is separated into a third retentate stream 75 and a third permeate stream 80. The third retentate stream 75 is combined with the feed stream 30 and the combined stream is then fed to the first purification stage 35. The third permeate stream 80 may be flared, vented, thermally oxidized, or recovered as a valuable $CO_2$ product gas.

Figure 2:
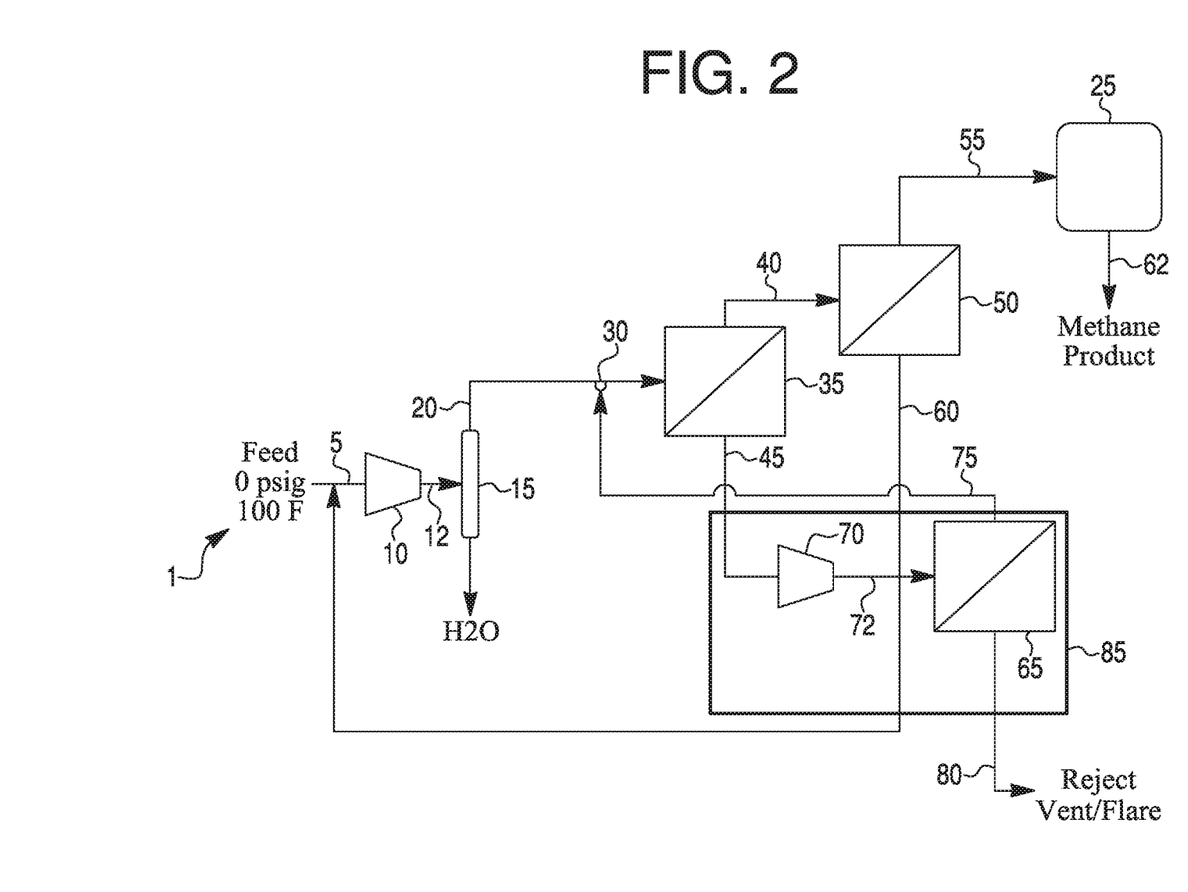
FIG. 2 illustrates a second embodiment of biomethane production containing a high recovery module and a $H_2S$ removal media.

Alternatively, as shown in FIG. 2, the $H_2S$ scavenger media 25 is placed downstream of the second purification stage 50 so as to remove remaining undesirable amounts of $H_2S$ from the second retentate stream 55. After treatment by the $H_2S$ scavenger media 25, a stream of biomethane product gas 62 is yielded that contains 4 ppm or less of $H_2S$ and 150 ppm or less of water.

While not illustrated in FIGS. 1-2, one of ordinary skill in the art can easily envisage an HRM that contains a first group of one or more membranes in series with a second group of one or more membranes where the first permeate stream 45 is separated by the first group into an intermediate permeate stream and an intermediate retentate stream. The intermediate retentate stream is separated by the second group into the third permeate stream and the third retentate stream. In this scenario, the intermediate permeate stream may be recovered as a useful $CO_2$ product gas and the third permeate stream is vented, flared or thermally oxidized at a thermal oxidation unit.

Prophetic Example

With reference to the process conditions shown in Table I, raw biogas stream (A) has the following gas composition: 6.69% by volume water, 100 ppm by volume $H_2S$, 32.08% by volume $CO_2$, and 61.23% by volume $CH_4$. After being combined with the second permeate stream, the combined stream (B) is compressed to 200 psig with a main compressor and subsequently dehydrated and also treated by $H_2S$ scavenger media to reduce the $H_2S$ down to trace levels. The reduced-$H_2S$ stream is combined with the third retentate stream (C) to yield a feed stream (D). This feed stream (D) is fed to the first purification stage where it is separated into a first permeate stream (E) and a first retetate stream. The first retentate stream is fed to the second purification stage where it is separated into a second permeate stream (which is combined with the raw biogas stream (A) upstream of the main compressor) and a stream of product biomethane (F). The first permeate stream (E) is fed to the HRM where it is first compressed and then separated by the third purification stage into a third permeate stream (G) and a third retentate stream (C) (which is combined with the reduced-$H_2S$ stream). pressures for first membrane stage 10 is 2 psig, and the first membrane permeate is pressurized to 210 psig then enters a third membrane stage of rubbery or glassy membranes. For membrane stages 65 and 50, the permeate pressures are 2 psig. The total gas flow for the biomethane 55 is 432 SCFM ($CO_2$ concentration is 2% by volume and $H_2S$ concentration is below 4 ppm). The material balance according to FIG. 1 is shown in Table 1.

TABLE 1

Process Conditions for Prophetic Example

| Diagram Label | A | B | C | D | E | F | G |
|---|---|---|---|---|---|---|---|
| Flow, SCFM | 694 | 949 | 42 | 948 | 261 | 432 | 217 |
| Pressure, psig | 0 | 0 | 200 | 200 | 2 | 150 | 2 |
| Temperature (° F.) | 100 | 100 | 100 | 100 | 100 | 100 | 100 |
| $CH_4$ (mol %) | 61.23 | 58.50 | 51.69 | 60.84 | 8.96 | 98.00 | 0.83 |
| $CO_2$ (mol %) | 32.08 | 36.51 | 48.27 | 38.67 | 89.63 | 2.00 | 98.57 |
| $H_2S$ (mol %) | 100 ppm | ~70 ppm | Trace | Trace | Trace | Trace | Trace |
| $H_2O$ (mol %) | 6.69 | 4.99 | 0.05 | 0.48 | 1.42 | Dry | 0.60 |

The invention provides several advantages.

A relatively high methane recovery (in the second retentate stream from the raw biogas stream) may be achieved at a capital expense that is lower than many conventional schemes such as the one disclosed by U.S. Pat. No. 8,999,038. In U.S. Pat. No. 8,999,038, biogas is purified in a cascaded manner in which the retentate from the feed stage is fed to the retentate stage, which is in turn yields the product biomethane. Because the low pressure permeate from the feed stage is fed to the permeate stage without first being compressed, the pressure difference across the membrane from the feed side to the permeate side (i.e., the driving force) is quite low. Since the driving force is quite low, a significantly greater number of membranes must be used in the permeate stage of U.S. Pat. No. 8,999,038.

In contrast, the fairly high mixed gas carbon dioxide/methane selectivities required by U.S. Pat. No. 8,999,038 (such as the selectivity of 45 described in the examples of U.S. Pat. No. 8,999,038) are not necessary in the instant invention. Because the first permeate stream is compressed (according to the invention) before it is fed to the third purification stage, there is a relatively high driving force across the membrane(s) of the third purification stage. Since the driving force is relatively high, a more moderate mixed gas carbon dioxide/methane selectivity is more than satisfactory for practicing the invention.

Also, although the invention requires the use of a compressor in the HRM, the cost of this secondary compressor is more than offset by two factors: 1) the reduced number of membranes required by the scheme of the invention, 2) the reduced size of the secondary compressor that need only have the capacity to compress a fairly low flow of gas from the first purification stage, and 3) the first stage permeate pressure can be higher than the raw gas pressure leading to a higher suction pressure and smaller compressor due to the resultant reduced compression pressure ratio In order to better illustrate the above point regarding the number of membranes required, computer simulations were performed comparing the three-stage scheme of U.S. Pat. No. 8,999,038 (which does not compress the feed stage permeate before being fed to the permeate stage) to the system according to the invention. The following assumptions were made about the U.S. Pat. No. 8,999,038 scheme: the carbon dioxide content of the raw biogas treated was 40%, the selectivity of the membranes was equal to 40, the 98.5% of the methane in the raw biogas was recovered in the biomethane product gas, and the carbon dioxide content of the biomethane product gas was only 0.38%. Based upon these assumptions, 36 membrane modules per 1 MM SCFD of raw biogas treated were required by the U.S. Pat. No. 8,999,038 scheme. Using the same assumptions (except for compression of the first permeate stream), only 16 modules per 1 MM SCFD of raw feed were required by the invention.

Thus, the number of membrane modules required dropped by 56%. Using the same assumptions (except for a more moderate selectivity of 16 and compression of the first permeate stream), only 11 modules per 1 MM SCFD of raw feed were required by the invention. Thus, the number of membrane modules required dropped by 69%.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A method of producing biomethane, comprising:
separating a feed stream containing methane and impurities at a first purification stage comprising at least one membrane selective for carbon dioxide over methane into a first retentate stream and a first permeate stream;
separating the first retentate stream at a second purification stage comprising at least one membrane selective for carbon dioxide over methane into a second retentate stream and a second permeate stream, the second retentate stream being a product stream comprising biomethane;
feeding the first permeate stream to a high recovery module comprising a second compressor and a third purification stage comprising one or more membranes in parallel or in series;
compressing the first permeate stream at the secondary compressor; and
separating the compressed first permeate stream at the third purification stage into a third retentate stream and a third permeate stream.

2. The method of claim 1, further comprising a step of feeding the second permeate stream and a raw biogas stream to a main compressor and compressing them so as to form a combined stream, the raw biogas stream comprising 40-75% methane and impurities of: greater than 0% and up to 10% nitrogen, greater than 0% and up to 3% oxygen, 20-55% carbon dioxide, greater than 0 ppm and up to 5,000 ppm hydrogen sulfide, 0 to 100 ppm siloxanes, greater than 0 ppm and up to 1,000-2,000 ppm of C6+ hydrocarbons and VOCs, and greater than 0% water.

3. The method of claim 2, wherein the first retentate stream comprises at least 60% methane, the first permeate stream comprises less than 20% methane, the second retentate stream comprises at least 94% methane, the second permeate stream comprises less than 80% methane, the third retentate stream comprises at least 40% methane.

4. The method of claim 3, wherein an amount of water is removed from the combined stream at a dehydration unit or through cooling after compression prior to combination with the third retentate stream.

5. The method of claim 2, further comprising the steps of:
feeding the second permeate stream and a raw biogas stream to a main compressor and compressing them so as to form a combined stream; and
forming the feed stream is formed by combining the third retentate stream with the combined stream, wherein the second permeate stream comprises at least 40% methane, at least 20% carbon dioxide, less than 1,000 ppm hydrogen sulfide, less than 1000 ppm of $C_{6+}$ hydrocarbons, VOCs and siloxane, and less than 0.05% water and the first permeate stream comprises 5-15% methane, greater than 0 ppm but up to 10,000 ppm of $H_2S$, greater than 0% but up to 3% water, and up to 95% $CO_2$.

6. The method of claim 4, wherein, after water removal at the dehydration unit and prior to combination with the third retentate stream, $H_2S$ levels in the combined stream are reduced to less than 4 ppm using $H_2S$ scavenger media.

7. The method of claim 5, further comprising the steps of:
feeding the combined stream to an adsorption-based purification unit where amounts of $C_{6+}$ hydrocarbons present in the combined stream are removed by the adsorption-based purification unit, the adsorption-based purification unit comprising an adsorbent bed, the adsorption-based purification unit being selected from the group consisting of a non-regenerative media unit, a pressure swing adsorption unit, a temperature swing adsorption unit, and a pressure-temperature swing adsorption unit; and
optionally, when the adsorption-based purification unit is a pressure swing adsorption unit, a temperature swing adsorption unit or a pressure-temperature swing adsorption unit, regenerating the adsorption bed with the third permeate stream.

8. The method of claim 1, wherein:
the third purification stage comprises a first group of one or more membranes that is in series with a second group of one or more membranes;
the first permeate stream is separated by the first group into an intermediate retentate stream and an intermediate permeate stream;
the intermediate retentate stream is fed to the second group where it is separated into the third permeate stream and the third permeate stream.

9. The method of claim 1, wherein each of said at least one membrane of said first purification stage comprises a porous polymeric substrate having at least one separation layer, the substrate being selected from the group consisting of polyimides, poly sulfones, polyether ether ketones, and mixtures thereof.

10. The method of claim 9, wherein the substrate is a polyether ether ketone.

11. The method of claim 9, wherein the separation layer is made of a copolymer or block polymer of the formula:

where PA is an aliphatic polyamide having 6 or 12 carbon atoms and PE is either poly(ethylene oxide) or poly(tetramethylene oxide).

12. The method of claim 9, wherein the separation layer is made of repeating units of the following monomers:

13. The method of claim 9, wherein the separation layer is made of a copolymer or block polymer of tetramethylene oxide, propylene oxide, and/or ethylene oxide.

14. The method of claim 1, wherein the at least one membrane of the first purification stage is also selective for $H_2S$, $C_{6+}$ hydrocarbons, siloxane and water over methane.

15. The method of claim 1, wherein the at least one membrane of the second purification stage is comprised of a material selected from the group consisting of cellulose acetate, a polysulfone, a polyimide, and mixtures thereof.

16. The method of claim 1, wherein a pressure differential over the membrane between the first permeate stream and the feed stream is less than 50 psig.

17. The method of claim 1, wherein the second permeate stream comprises at least 40% methane, at least 20% carbon dioxide, less than 1,000 ppm hydrogen sulfide, less than 1000 ppm of $C_{6+}$ hydrocarbons and siloxane, and less than 0.05% water.

18. The method of claim 1, wherein the first permeate stream comprises 5-15% methane, greater than 0 ppm but up to 10,000 ppm of $H_2S$, greater than 0% but up to 3% water, and up to 95% $CO_2$.

19. The method of claim 1, further comprising the steps of compressing the second permeate stream and a raw biogas stream at a main compressor so as to form a combined stream and forming the feed stream by combining the third retentate stream with the combined stream, wherein the raw biogas stream has a methane concentration of 40-75% and at least 98% of methane in the raw biogas stream is recovered in the second retentate stream.

20. The method of claim 1, wherein the at least one membrane of the third stage is the same as the at least one membrane of the first stage.

21. The method of claim 1, wherein the at least one membrane of the third stage is the same as the at least one membrane of the second stage.

22. The method of claim 1, wherein said product stream is comprised of at least 94% methane, below 3% of $CO_2$, below 150 ppm of $H_2S$, below 100 ppm of VOC's, and below 0.01% of $H_2O$.

23. The method of claim 1, further comprising the step of removing amounts of $H_2S$ from the second retentate stream with a $H_2S$ scavenger media so as to achieve a $H_2S$ concentration in the second retentate stream of less than 4 ppm of $H_2S$.

* * * * *